(12) United States Patent
Bar-On

(10) Patent No.: US 8,052,705 B2
(45) Date of Patent: Nov. 8, 2011

(54) INSTRUMENT AND METHOD FOR SCRUBBING THE CORNEAL EPITHELIUM

(76) Inventor: Yariv Bar-On, Rishon Lezion (IL)

(*) Notice: Subject to any disclaimer, the term of this patent is extended or adjusted under 35 U.S.C. 154(b) by 91 days.

(21) Appl. No.: 11/673,604

(22) Filed: Feb. 12, 2007

(65) Prior Publication Data

US 2008/0195127 A1    Aug. 14, 2008

(51) Int. Cl.
*A61F 9/00* (2006.01)
(52) U.S. Cl. .......... 606/161; 606/166
(58) Field of Classification Search ......... 606/160, 606/161, 162, 166; 216/11; 433/51, 54, 433/61, 62; 30/27, 535, 169–172; 604/294; 15/236.01, 236.05–236.07, 245, 245.1; D24/133, D24/146, 150, 172
See application file for complete search history.

(56) References Cited

U.S. PATENT DOCUMENTS

| | | | | |
|---|---|---|---|---|
| 892,316 A * | 6/1908 | Schwartz et al. | | 30/27 |
| 1,574,666 A * | 2/1926 | Lynch | | 15/245 |
| 3,436,823 A * | 4/1969 | Lamb et al. | | 30/169 |
| 4,898,170 A * | 2/1990 | Hofmann et al. | | 606/166 |
| 5,426,809 A * | 6/1995 | Muta | | 15/228 |
| 5,649,943 A | 7/1997 | Amoils | | |
| 5,792,160 A | 8/1998 | Weiss et al. | | |
| 5,916,228 A * | 6/1999 | Ripich et al. | | 606/161 |
| 6,565,586 B2 * | 5/2003 | Harrold et al. | | 606/166 |
| 6,679,897 B2 * | 1/2004 | Josephson | | 606/160 |
| 7,141,048 B1 | 11/2006 | Charles | | |
| 2002/0065532 A1 * | 5/2002 | Harrold et al. | | 606/166 |
| 2005/0065539 A1 * | 3/2005 | Muser | | 606/161 |
| 2005/0228419 A1 * | 10/2005 | El-Mansoury | | 606/166 |
| 2006/0047255 A1 * | 3/2006 | Kiehlbauch et al. | | 604/294 |
| 2006/0259053 A1 * | 11/2006 | El-Mansoury | | 606/166 |

* cited by examiner

*Primary Examiner* — Ryan Severson
*Assistant Examiner* — David Eastwood
(74) *Attorney, Agent, or Firm* — Mark M. Friedman

(57) ABSTRACT

A scrubbing instrument for scrubbing the human eye corneal epithelium, including a handle, having a grip portion, a scrubbing head having a curved main scrubbing surface, and a connection arrangement for enabling connection of the scrubbing head to the handle and disconnection of the scrubbing head from the handle, thus enabling the scrubbing head to serve as a sterile, disposable, single-use component.

17 Claims, 4 Drawing Sheets

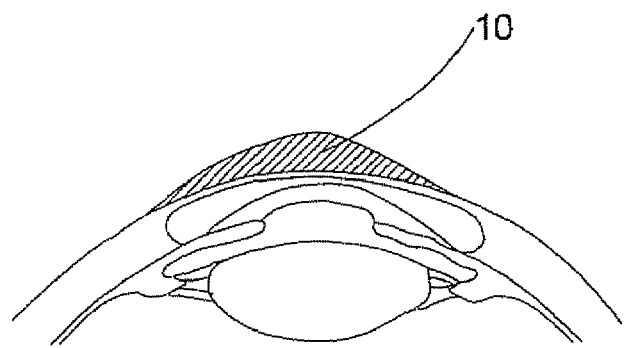
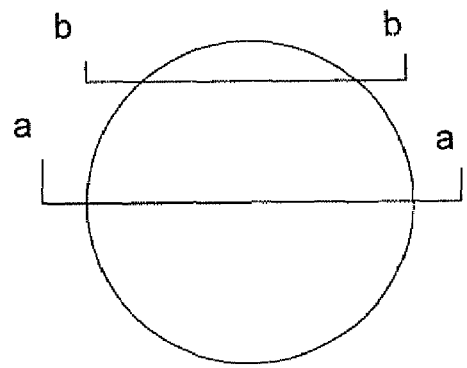
FIG.1a
FIG.1c
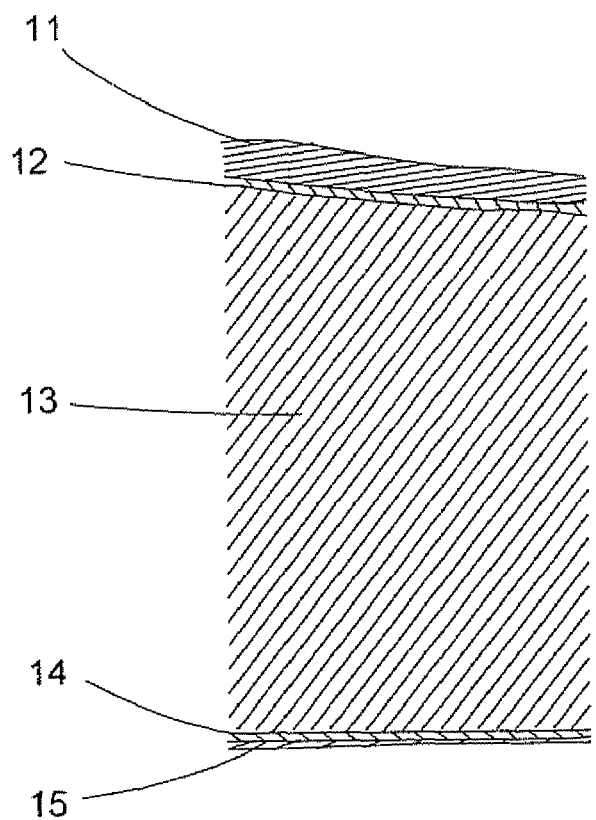
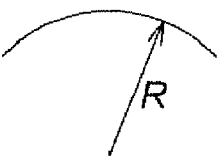
FIG.1d
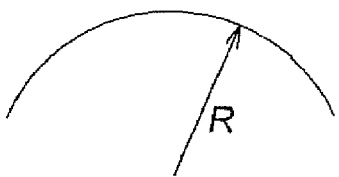
FIG.1e
FIG.1b

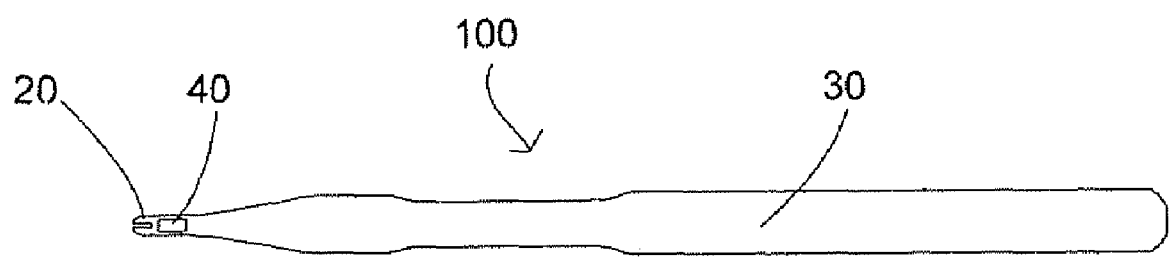
FIG. 2a
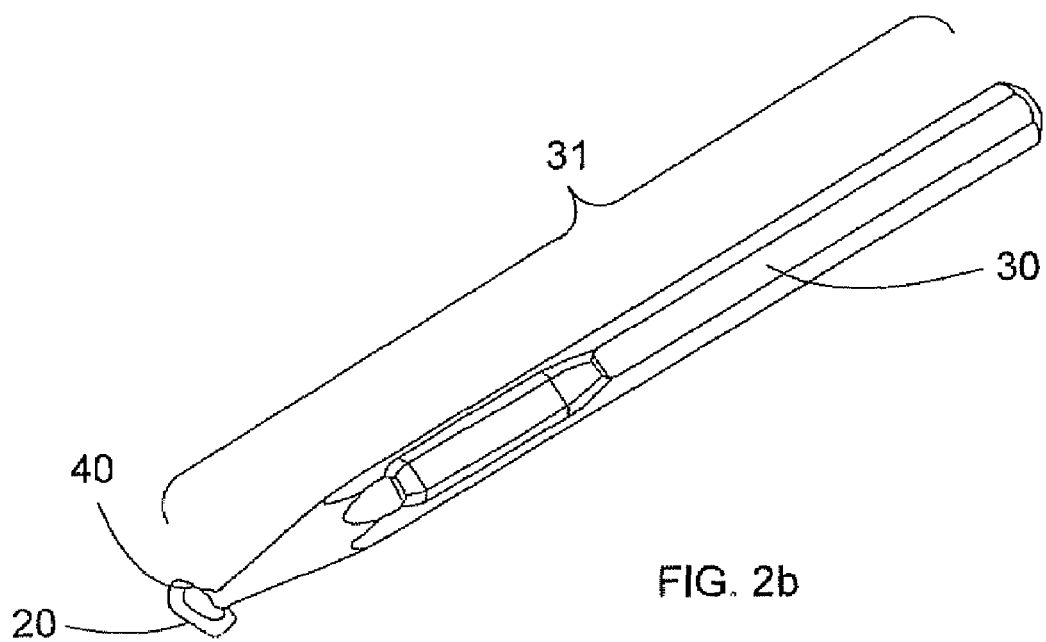
FIG. 2b
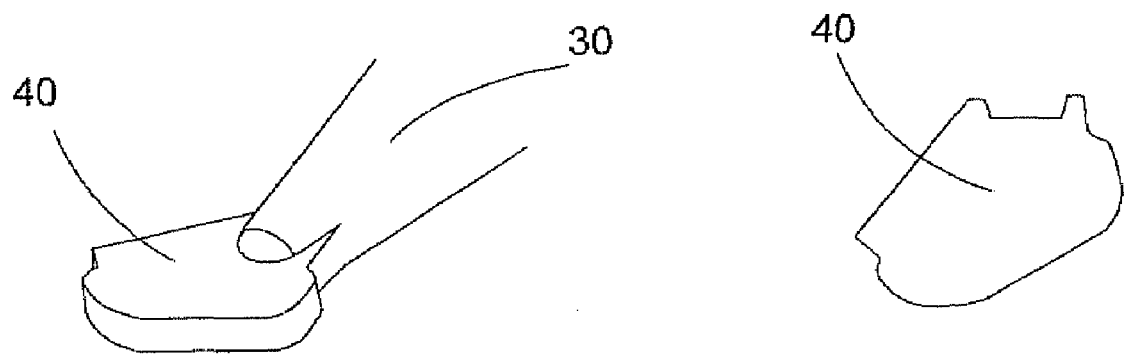
FIG. 3a
FIG. 3b

INSTRUMENT AND METHOD FOR SCRUBBING THE CORNEAL EPITHELIUM

FIELD AND BACKGROUND OF THE INVENTION

The present invention relates to an instrument and a method for scrubbing the human eye corneal epithelium.

A high percentage of the population suffers various vision defects, including focusing (refractive) defects such as short-sightedness, long-sightedness and astigmatism. Refractive defects are usually corrected by wearing eyeglasses or contact lenses.

Refractive defects are caused by an imperfect three-dimensional spatial structure of the cornea and the eye bulb size, erg. myopia, a near-sightedness resulting from the elongation of the eyeball so that parallel rays are focused in front of the retina, or hyperopia, a far-sightedness, resulting from an error of refraction in which rays of light entering the eye are brought into focus behind the retina.

Avoiding the need for wearing eyeglasses or contact lenses is made possible by reshaping the shape of the exterior surface of the cornea.

At present, several surgical technical methods are used to treat refractive errors, the most reliable treatment using laser tools.

Removal of the epithelium is usually done by means of manual scrubbing using a scrubbing tool or blade. The scrubbing tools currently in use are crude tools, for multiple use, are usually made of one piece of rust-free metal, such as stainless steel, and have a shape resembling that of a golf club, with a planar scrubbing surface. These tools have many drawbacks as a result of their structure, including repetitive scraping of the scrubbing surface as a result of repeated use, discomfort in holding the tool, the fact that the tool is highly traumatic to the cornea, especially to the stroma layer, and can even scratch the cornea when used without care, and can also be contaminated, thus requiring sterilization between uses, as well as the very grave drawback of the planar scrubbing surface applying pointed pressure on the cornea.

There is therefore the need for a scrubbing tool, whose scrubbing surface is a curved surface adapted to the shape of the cornea, and is intended for single use.

The prior art does not teach or suggest such a tool.

SUMMARY OF THE INVENTION

According to the present invention there is provided an instrument and a method for scrubbing the human eye corneal epithelium, with a curved scrubbing surface with a spatial form well-adapted to the shape of the surface of the patient's cornea, which is a component of a tool intended for single use, and can be assembled on a handle intended for repeated use, for performing scrubbing of the cornea as a preliminary stage prior to the refractive laser procedure known as ablation, for the purpose of performing procedures such as Photo Refractive Keratectomy (PRK), Photo Therapeutic Keratectomy (PTK), Laser in situ Keratomileusis (EPILASIK), and all Advanced Surface Ablation (ASA) techniques.

The instrument for scrubbing the human eye corneal epithelium according to the present invention enables removal of the Bowman's layer; however it also has qualities that enable its use without damaging the Bowman's layer.

The instrument for scrubbing the human eye corneal epithelium according to the present invention enables multipurpose scrubbing of the epithelium in a manner that is friendly to both patient and practitioner Its qualities include that it does not cause trauma to the cornea's stroma layer at the extent usually inflicted by scrubbing with standard tools, its use is highly convenient and enables applying uniform working pressure on the cornea during engraving, it enables scraping foreign objects from the cornea and scraping and removing scarring from the cornea (by changing the instrument for scrubbing the human eye corneal epithelium according to the present invention to a specific scrubbing device for these applications, different scrubbing devices are used for different applications), it is sterile and precise and suitable for use by any expert of standard knowledge in the field, and it is composed of biocompatible materials and is harmless to the cornea during treatment.

Additional objects and advantages of the invention will be set forth in part in the description which follows and, in part, will be obvious from the description, or may be learned by practice of the invention.

1. The scrubbing instrument according to the present invention can also be changed for the purpose of other intended uses such as extraction of foreign bodies, or other practices which will be developed in the future 2. The instrument can be completely disposable or disposable only in part (such as the scrubbing head).

3. The scrubbing instrument can be entirely composed of biocompatible polymers.

4. There can be at least three different scrubbing instruments with at least three different radii for the application described here alone.

5. The scrubbing instrument is disposable and can be designated for single use.

According to the present invention there is provided a scrubbing instrument for scrubbing the human eye corneal epithelium, the scrubbing instrument including: (a) a handle, having a grip portion; (b) a scrubbing head having a curved main scrubbing surface; and (c) a connection arrangement for enabling connection of the scrubbing head to the handle and disconnection of the scrubbing head from the handle, thus enabling the scrubbing head to serve as a sterile, disposable, single-use component.

According to still further features in the described preferred embodiments, the scrubbing instrument has a center of gravity, and the scrubbing head includes a virtual Cartesian coordinate system having an x-axis, a y-axis, and a z-axis intersecting at an origin, wherein the origin is substantially in the same location of the center of gravity, wherein the z-axis is substantially orthogonal to the curved main scrubbing surface at a point where the z-axis passes through the curved main scrubbing surface, wherein the y-axis defines a direction of scrubbing motion, wherein the x-axis and the z-axis define a xz plane, wherein the curved main scrubbing surface has a local curve radius at the point on the xz plane, wherein the y-axis and the z-axis defines a yz plane, and wherein the curve radius is of at least 6 millimeters and at most 10 millimeters.

According to still further features in the described preferred embodiments the scrubbing surface includes no metallic compound.

According to still further features in the described preferred embodiments the scrubbing head includes: (i) a draining groove, for draining excess scrubbed tissue, located inside the scrubbing head, having an opening through the curved main scrubbing surface.

According to still further features in the described preferred embodiments the scrubbing head further includes: (ii) a draining channel for better draining of excess scrubbed tissue, wherein the draining channel is disposed in the draining groove.

According to still further features in the described preferred embodiments the scrubbing has at least one secondary scrubbing surface.

According to still further features in the described preferred embodiments the handle has a first end and the connection arrangement is a connector, wherein the connector is disposed at the first end of the handle.

According to still further features in the described preferred embodiments the handle has a virtual central longitudinal axis, wherein the angle between the longitudinal axis and the z-axis on the yz plane is of at least 0 degrees and at most 10 degrees.

According to still further features in the described preferred embodiments the handle has a virtual central longitudinal axis, wherein the angle between the longitudinal axis and the z-axis on the yz plane is of at least 10 degrees and at most 20 degrees.

According to still further features in the described preferred embodiments the handle has a virtual central longitudinal axis, wherein the angle between the longitudinal axis and the z-axis on the yz plane is of at lest 20 degrees and at most 30 degrees.

According to still further features in the described preferred embodiments the handle has a virtual central longitudinal axis, wherein the angle between the longitudinal axis and the z-axis on the yz plane is of at lest 30 degrees.

According to still further features in the described preferred embodiments the handle has a virtual central longitudinal axis, wherein the angle between the longitudinal axis and the z-axis on the xz plane is of at least 0 degrees and at most 10 degrees.

According to the present invention there is provided a method of scrubbing the human eye corneal epithelium, the method of scrubbing including the steps of t (a) providing a scrubbing instrument including: (i) a handle, having a grip portion; (ii) a scrubbing head having a curved main scrubbing surface; and (iii) a connecting arrangement for enabling connection of the scrubbing head to the handle and disconnection of the scrubbing head from the handle, thus enabling the scrubbing head to serve as a sterile, disposable, single-use components; (b) gently placing the scrubbing instrument on the human eye, causing the curved main scrubbing surface to touch an area of the corneal epithelium, wherein the touching area has a dimension of at least 10 square millimeters; and (c) performing scrubbing motion.

According to still further features in the described preferred embodiments the method further including the steps of: (d) disconnecting the scrubbing head from the handle, According to still further features in the described preferred embodiments of the method, the scrubbing surface includes no metallic compound.

According to still further features in the described preferred embodiments the method further including the steps of: (e) connecting a new scrubbing head to said handle.

BRIEF DESCRIPTION OF THE DRAWINGS

The invention is herein described, by way of example only, with reference to the accompanying drawings, wherein:

FIG. 1a illustrates a section of the anterior of the human eye.

FIG. 1b illustrates a section of the layers of the human eye cornea

FIGS. 1c-1e illustrate local curve radii of a cornea,

FIG. 2a is a schematic illustration of a side view of a preferred embodiment of an instrument for scrubbing the human eye corneal epithelium according to the present invention.

FIG. 2b is a schematic illustration of an isometric view of a preferred embodiment of an instrument for scrubbing the human eye corneal epithelium according to the present invention.

FIG. 3a is schematic illustration of an isometric view of a magnified view showing the connection of a handle to a connector, according to a preferred embodiment of an instrument for scrubbing the human eye corneal epithelium according to the present invention FIG. 3b is schematic illustration of a front view of a connector according to a preferred embodiment of an instrument for scrubbing the human eye corneal epithelium according to the present invention.

DESCRIPTION OF THE PREFERRED EMBODIMENTS

Figure 4A:
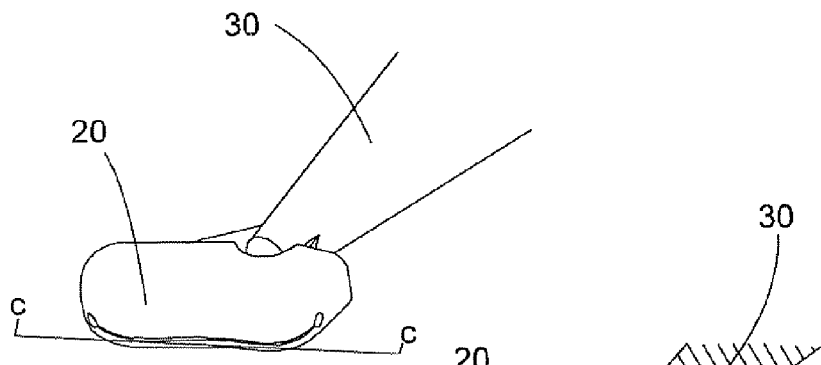
FIG. 4a is a schematic illustration of an isometric view of a magnified detail showing the connection of a handle to a scrubbing head according to a preferred embodiment of an instrument for scrubbing the human eye corneal epithelium according to the present invention, showing the connector.

The present invention is an instrument and a method for scrubbing the human eye corneal epithelium.

The principles and operation of the instrument for scrubbing the human eye corneal epithelium, according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

The following list is a legend of the numbering of the application illustrations:

10 cornea
11 epithelium
12 Bowman's layer
13 stroma
14 Descemet's membrane
15 endothelium
20 scrubbing head
22 draining groove
23 draining channel
24 connector applicator
26 main scrubbing surface
27 first secondary scrubbing surface
28 second secondary scrubbing surface
30 handle
31 grip portion
40 connector
100 scrubbing instrument
R local curve radius (of a curve of a scrubbing surface at a section)

Referring now to the drawings;

FIG. 1a illustrates a section of the anterior of the human eye. The illustration shows cornea 10.

The cornea is a clear anterior window of the human eye that transmits and refracts light into the eye.

FIG. 1b illustrates a section of the five layers of the human eye cornea.

The external layer, the first, which is in contact with the environment, is the epithelium 11 layer, which is between 50 micrometers (microns) and 70 microns thick.

The epithelium layer blocks the passage of foreign materials into the eye and provides a smooth surface, and is filled with tiny nerves If this layer is damaged, it tends to renew itself The second layer is the Bowman's layer 12, which is 5-7 microns thick. The third layer is the stroma layer 13, which is approximately 500 microns thick. The fourth layer is the Descemet's membrane layer 14, which is 3-5 microns thick. The thicknesses of all five layers as noted are typical for a healthy adult, at the central point at which each layer is thickest.

FIG. 1c is a schematic illustration of a top view of a cornea, marked with two section lines, a-a and b-b.

FIG. 1d shows local radius R at a point upon the curve of the corneal surface, on the anterior side, a curve on the plane of section a-a passing approximately through the center of the cornea The average local radius of the cornea of an adult at the center of the cornea is approximately 7.8 millimeters.

FIG. 1e shows local radius R at a point upon the curve of the corneal surface, on the anterior side, a curve on the plane of section b-b. This local radius can differ in its dimensions from those of the local radius described with regard to section a-a. The average local radius of the cornea of an adult at its periphery is approximately 8.8 millimeters.

FIG. 2a is a schematic illustration of a side view of a preferred embodiment of an instrument for scrubbing the human eye corneal epithelium 100 according to the present invention. Scrubbing instrument 100 includes handle 30, connector 40 and scrubbing head 20.

Disposable scrubbing head 20 is mounted through a suitable rigid coupling means or connecting arrangement, such as a frictionally-engaged sliding track mechanism. The coupling or connector arrangement can be in the form of a socket and a plug that are detachable from one another.

FIG. 2b is a schematic illustration of an isometric view of a preferred embodiment of an instrument for scrubbing the human eye corneal epithelium 100 according to the present invention. In one preferred embodiment, handle 30 consists of a grip portion 31 and at one end, and a connector 40 for connecting disposable scrubbing head 20. Namely, connector 40 can be an integral part of handle 30, but can also be a separate part which connects to handle 30.

FIGS. 3a is a schematic illustration of an isometric view of a magnified detail showing, the connection of handle 30 to connector 40, according to a preferred embodiment of an instrument for scrubbing the human eye corneal epithelium according to the present invention.

FIG. 3b is a schematic illustration of a front view of a connector 40 according to a preferred embodiment of an instrument for scrubbing the human eye corneal epithelium according to the present invention.

FIG. 4a is a schematic illustration of an isometric view of a magnified detail showing the connection of handle 30 to scrubbing head 20, according to a preferred embodiment of an instrument for scrubbing the human eye corneal epithelium according to the present invention. The illustration shows section line c-c.

Figure 4B:
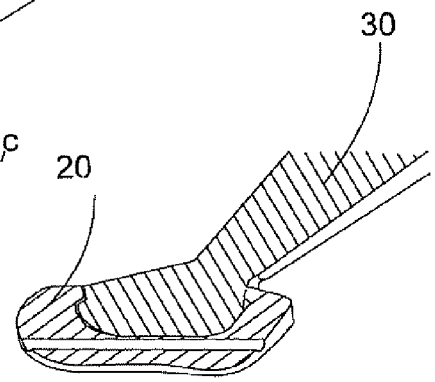
FIG. 4b is a schematic illustration of an isometric view, in section, of a magnified detail showing the connection of a handle to a scrubbing head according to a preferred embodiment of an instrument for scrubbing the human eye corneal epithelium according to the present invention, showing the connector.

FIG. 4b is a schematic illustration of an isometric view along section c-c of a magnified detail showing the connection of handle 30 to scrubbing head 20, according to a preferred embodiment of an instrument for scrubbing the human eye corneal epithelium according to the present invention, showing the connector.

Figure 4C:
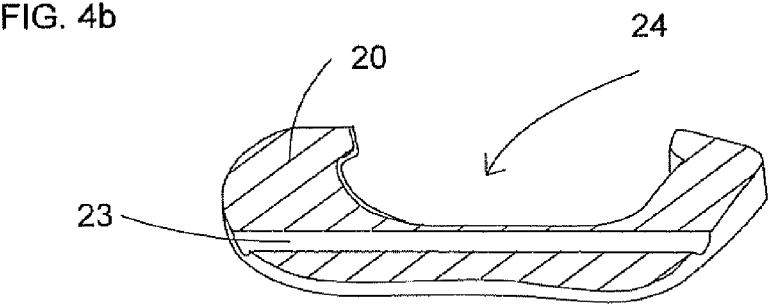
FIG. 4c is a schematic illustration of an isometric view, in section, of a magnification of the scrubbing head according to a preferred embodiment of an instrument for scrubbing the human eye corneal epithelium according to the present invention, showing the connector.

FIG. 4c is a schematic illustration of an isometric view along section c-c of a magnification of the scrubbing head 20, according to a preferred embodiment of an instrument for scrubbing the human eye corneal epithelium according to the present invention, showing the connector. The illustration also shows draining channel 23, serving to drain excess scrubbed tissue, as well as connector applicator 24, into which connector 40 is inserted with force and held with pressure connector 40, as one possible method of connection.

Figure 4D:
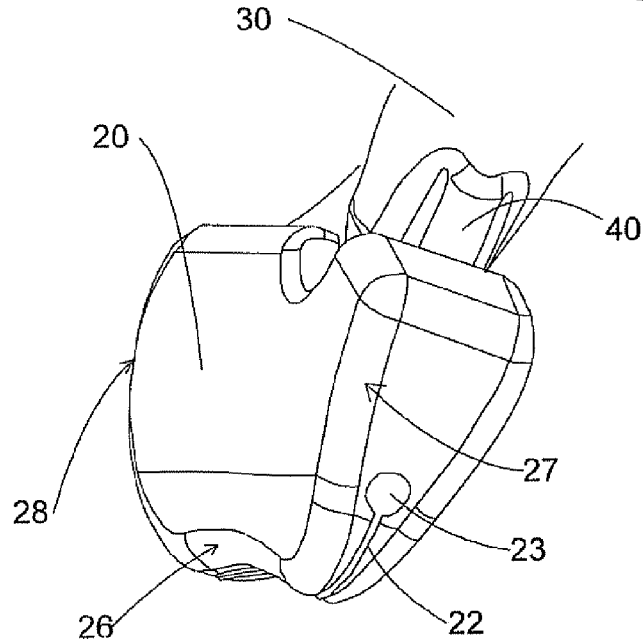
FIG. 4d is a schematic illustration of an isometric view of an additional magnification of the scrubbing head according to a preferred embodiment of an instrument for scrubbing the human eye corneal epithelium according to the present invention, showing the connector.

FIG. 4d is a schematic illustration of an isometric view of an additional magnification of scrubbing head 20, according to a preferred embodiment of an instrument for scrubbing the human eye corneal epithelium according to the present invention, showing the connector.

Scrubbing the human eye corneal epithelium according to the present invention is done with physical contact between the scrubbing head 20 and the cornea, with scrubbing motion. The geometrical shape of the scrubbing instrument 100 has curved face surfaces of variable curves, namely with varying local radii R along their section lines.

Selection of the geometrical shapes of the face surfaces of the scrubbing head 20 during its design is done to enable creation of a large contact surface in comparison with the point of local contact made during use of an scrubbing instrument with a planar contact surface. Scrubbing heads 20 can be designed and manufactured in various shapes and sizes so that the practitioner performing the scrubbing can select the one most suitable for performing the scrubbing according to the size and shape of the patient's corneal surface, and can select the contact area of the scrubbing head 20 according to the area of the patient's corneal surface during the actual scrubbing procedure.

According to one preferred embodiment of the present invention, scrubbing head 20 includes three scrubbing surfaces: a main scrubbing surface 26; a first secondary scrubbing surface 27; and a second secondary scrubbing surface 28. At the bottom of scrubbing head 20 a draining groove 22 can optionally be disposed, the end of which can be flared, for example in the form of draining channel 23, all for the purpose of draining excess engraved tissue. In FIGS. 4a-d, draining groove 22 is shown extending continuously along the entire length of main scrubbing surface 26 so as to subdivide the width of the main scrubbing surface.

An additional important quality of the scrubbing instrument 100 is the type of material or materials of which the scrubbing heads 20 are composed According to the present invention, the material or materials are biocompatible, and can be selected from a group of materials also including all plastic materials which are biocompatible with the cornea, with suitable hardness levels.

The scrubbing heads 20 can be made of one material, or of several materials with varying levels of hardness, for example in a tiered structure The scrubbing heads 20 can have a depression or other suitable mechanism enabling connection to and disconnection from the handle, thus enabling them to serve as sterile, disposable, single-use components.

The scrubbing instrument 100 can of course be designed and manufactured to be completely disposable and single-use.

Furthermore, handle 30 can be designed with various shapes and sizes of the grip portion 31 for the purpose of optimal compatibility with the practitioner's hand. The structure of the scrubbing head 20 according to the present invention can also include a draining groove which enables effectively draining most of the substances in the engraved layers.

Figure 4E:
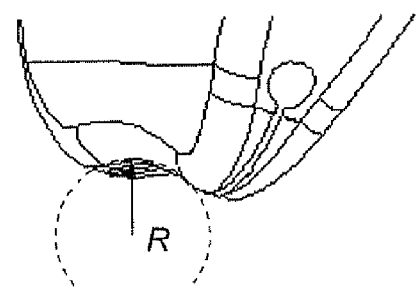
FIG. 4e is a schematic illustration of an isometric view of a detail of the scrubbing head indicating a local curve radius according to a preferred embodiment of an instrument for scrubbing the human eye corneal epithelium according to the present invention, showing the connector.
Figure 5A:
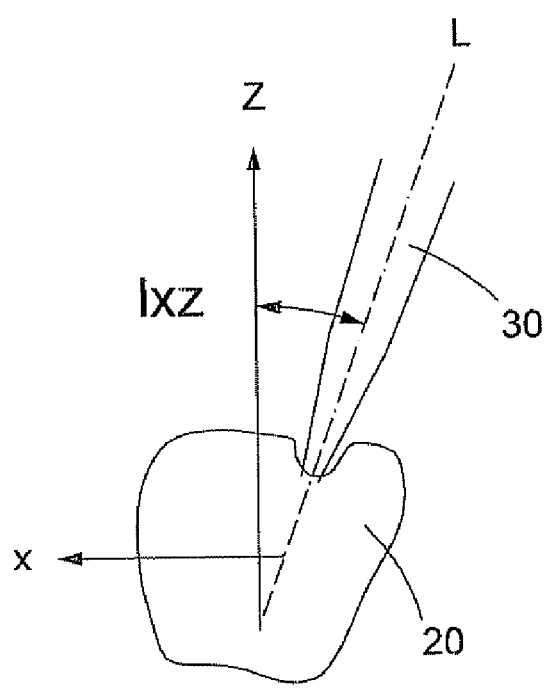
FIGS. 5a and 5b are schematic illustration of front and side views showing angles between the scrubbing head and the handle according to a preferred embodiment of an instrument for scrubbing the human eye corneal epithelium according to the present invention.
Figure 5B:
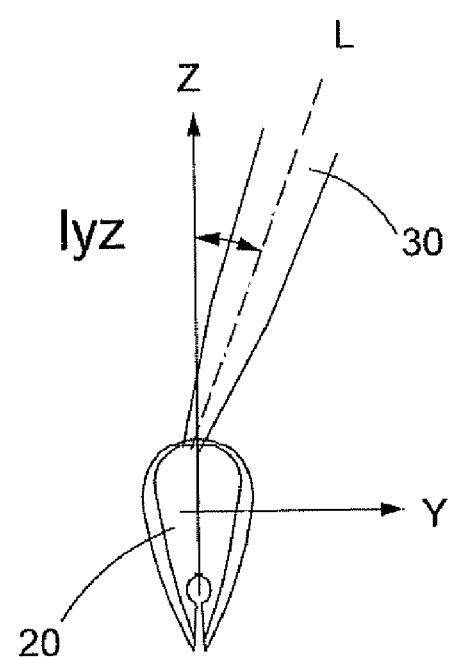

FIG. 4e is a schematic illustration of an isometric view of a detail of the scrubbing head 20 indication local curve radius R, according to a preferred embodiment of an instrument for scrubbing the human eye corneal epithelium according to the present invention, showing the connector FIGS. 5a and 5b are schematic illustrations of front and side views showing angles between the scrubbing head 20 and the handle 30, according to a preferred embodiment of an instrument for scrubbing the human eye corneal epithelium according to the present invention. Scrubbing head 20 is fixed to a three-dimensional XYZ Cartesian coordinate system, whose origin can be at the center of gravity of the scrubbing head 20 and its coordinate Z is facing upwards (when the bottom side of scrubbing head 20 is the side on which the main scrubbing surface 26 is disposed), as shown in both illustrations Handle 30 has a central longitudinal axis marked L in the illustrations.

FIG. 5a defines angle LXZ as an angle on plane XZ measured between longitudinal axis L and coordinate Z.

FIG. 5b defines angle LXY as an angle on plane XY measured between longitudinal axis L and coordinate Y.

Various models of the scrubbing instrument 100 can be designed so that the angles LXZ and LXY can be selected, for example, from a group of angles such as 10, 25, 30, or 40 degrees, etc.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A scrubbing instrument for scrubbing the human eye corneal epithelium, said scrubbing instrument comprising:
    (a) a handle, having a grip portion;
    (b) a scrubbing head formed from non-metallic material and having a curved main scrubbing surface, said scrubbing head having a first dimension and a second dimension perpendicular to said first dimension, said first dimension being greater than said second dimension; and
    (c) a connection arrangement for enabling connection of said scrubbing head to said handle and disconnection of said scrubbing head from said handle, thus enabling said scrubbing head to serve as a sterile, disposable, single-use component,
    wherein said main scrubbing surface has a width and has a length greater than said width, said length extending along a major part of said first dimension of said scrubbing head, and wherein said scrubbing head further comprises a continuous groove subdividing said main scrubbing surface, said groove defining at least part of a volume for receiving scrubbed tissue within the volume of said scrubbing head, wherein said groove extends entirely along said length so as to subdivide said main scrubbing surface across said width, wherein said scrubbing instrument further comprises a channel formed in said scrubbing head so as to define a contiguous volume with said groove, said channel extending substantially parallel to said first dimension of said scrubbing head, wherein said channel has a channel width measured parallel to said second dimension of said scrubbing head and said groove has a groove width measured parallel to said second dimension of said scrubbing head at an intersection of said groove with said main scrubbing surface, said channel width being greater than said groove width.

2. The scrubbing instrument of claim 1, wherein said channel intersects with said groove, said channel defining an additional part of said volume for receiving scrubbed tissue.

3. The scrubbing instrument of claim 2, wherein said scrubbing head has at least one secondary scrubbing surface.

4. A scrubbing instrument for scrubbing the human eye corneal epithelium, said scrubbing instrument comprising:
    (a) a scrubbing head formed from non-metal material, said scrubbing head having a first dimension and a second dimension perpendicular to said first dimension, said first dimension being greater than said second dimension, said scrubbing head having a scrubbing surface with a width and with a length greater than said width, said length extending along a major part of said first dimension of said scrubbing head; and
    (b) a continuous groove subdividing said scrubbing surface, said groove defining at least part of a volume for receiving scrubbed tissue within the volume of said scrubbing head, wherein said groove extends entirely along said length so as to subdivide said scrubbing surface across said width,
    wherein said scrubbing instrument further comprises a channel formed in said scrubbing head so as to define a contiguous volume with said groove, said channel extending substantially parallel to said first dimension of said scrubbing head, wherein said channel has a channel width measured parallel to said second dimension of said scrubbing head and said groove has a groove width measured parallel to said second dimension of said scrubbing head at an intersection of said groove with said scrubbing surface, said channel width being greater than said groove width.

5. The scrubbing instrument of claim 4, wherein said channel intersects with said groove, said channel defining an additional part of said volume for receiving scrubbed tissue.

6. The scrubbing instrument of claim 4, wherein said scrubbing head is formed from plastic material.

7. The scrubbing instrument of claim 4, further comprising a reusable handle releasably interconnectable with said scrubbing head.

8. The scrubbing instrument of claim 4, wherein said scrubbing surface has a contact surface of at least 10 square millimeters.

9. A method of scrubbing the corneal epithelium of the human eye, the method comprising the steps of:
  (a) providing a scrubbing instrument comprising:
    (i) a scrubbing head formed from non-metal material, said scrubbing head having a first dimension and a second dimension perpendicular to said first dimension, said first dimension being greater than said second dimension, said
    scrubbing head having a scrubbing surface with a width and with a length greater than said width, said length extending along a major part of said first dimension of said scrubbing head, and
    (ii) a continuous groove subdividing said scrubbing surface, said groove defining at least part of a volume for receiving scrubbed tissue within the volume of said scrubbing head, wherein said groove extends entirely along said length so as to subdivide said scrubbing surface across said width, wherein said scrubbing instrument further comprises a channel formed in said scrubbing head so as to define a contiguous volume with said groove, said channel extending substantially parallel to said first dimension of said scrubbing head, wherein said channel has a channel width measured parallel to said second dimension of said scrubbing head and said groove has a groove width measured parallel to said second dimension of said scrubbing head at an intersection of said groove with said scrubbing surface, said channel width being greater than said groove width;
  (b) placing said scrubbing instrument on the human eye with the scrubbing surface in contact with an area of the corneal epithelium; and
  (c) moving said scrubbing instrument in a scrubbing motion.

10. The method of claim 9, wherein said channel formed in said scrubbing head intersects with said groove, said channel defining an additional part of said volume for receiving scrubbed tissue.

11. The method of claim 9, wherein said scrubbing head is formed from plastic material.

12. The method of claim 9, wherein said scrubbing surface having a contact area of at least 10 square millimeters.

13. The method of claim 9, wherein said scrubbing instrument further comprises a reusable handle releasably interconnectable with said scrubbing head.

14. The method of claim 13, further comprising:
  (a) disconnecting said scrubbing head from said reusable handle; and
  (b) connecting a new scrubbing head to said reusable handle.

15. The scrubbing instrument of claim 1, wherein at least part of said main scrubbing surface has a convex curvature.

16. The scrubbing instrument of claim 4, wherein at least part of said scrubbing surface has a convex curvature.

17. The method of claim 9, wherein at least part of said scrubbing surface has a convex curvature.

* * * * *